United States Patent [19]
Black

[11] Patent Number: 6,043,223
[45] Date of Patent: Mar. 28, 2000

[54] ENHANCED OPENING OF ABNORMAL BRAIN TISSUE CAPILLARIES

[75] Inventor: Keith L. Black, Los Angeles, Calif.

[73] Assignee: The Regents of the University of California, Oakland, Calif.

[21] Appl. No.: 08/968,169

[22] Filed: Nov. 12, 1997

[51] Int. Cl.⁷ .......................... A61K 38/00; A61K 38/08
[52] U.S. Cl. .................. 514/15; 514/261; 514/79; 514/48; 514/17; 536/26.11; 435/240.242; 435/240.243; 435/240.241; 435/240.23; 435/240.24
[58] Field of Search ............... 514/15, 17; 435/240.242, 435/240.243, 240.241, 240.23, 240.24; 536/26.11

[56] References Cited

U.S. PATENT DOCUMENTS

| | | | |
|---|---|---|---|
| 5,260,210 | 11/1993 | Rubin et al. | 435/240.23 |
| 5,268,164 | 12/1993 | Kozarich et al. | 424/9 |
| 5,434,137 | 7/1995 | Black | 514/15 |
| 5,527,778 | 6/1996 | Black | 514/15 |
| 5,604,198 | 2/1997 | Poduslo et al. | 514/6 |
| 5,728,705 | 3/1998 | Lawson et al. | 514/261 |

OTHER PUBLICATIONS

Marrian Webster's Collegiate Dictionary, 10th ed; 1996, p. 748.

Nakano, S., Matsukado, K. and Black K.L., "Increased Brain Tumor Microvessel Permeability After Intracarotid Bradykinn Infusion Is Mediated by Nitric Oxide," Cancer Research 56, 4027–4031 (1996).

*Primary Examiner*—F. T. Moezie
*Attorney, Agent, or Firm*—Oppenheimer Wolff & Donnelly

[57] ABSTRACT

Improved compositions and methods for increasing permeability of abnormal brain tissue to pharmaceutical agents. Cyclic GMP specific phosphodiesterase inhibitors are combined with bradykinin or a bradykinin analog to provide enhanced permeability of brain capillaries which is limited to abnormal brain tissue. Neuropharmaceutical and neurodiagnostic agents introduced into the bloodstream are directed selectively to the abnormal brain tissue. The pharmaceutical preparation composed of bradykinin or a bradykinin analog and a cyclic GMP specific phosphodiesterase inhibitor may be administered either intravenously or directly into the carotid artery.

20 Claims, 5 Drawing Sheets

ENHANCED OPENING OF ABNORMAL BRAIN TISSUE CAPILLARIES

This invention was made with Government support under Grant No. NS25554 and Grant No. NS32103 awarded by the National Institute of Health (NIH). The Government has certain rights in this invention.

BACKGROUND OF THE INVENTION

1. Field of the Invention

The present invention relates generally to methods and compositions which are useful in selectively introducing pharmaceutical or diagnostic agents into abnormal brain tissue. More particularly, the present invention involves methods and compositions which selectively increase the permeability of the blood-brain barrier in abnormal brain tissue to provide for directed delivery of pharmaceutical or diagnostic agents to such abnormal tissue.

2. Description of the Related Art

The publications and other reference materials referred to herein to describe the background of the invention and to provide additional detail regarding its practice are hereby incorporated by reference. For convenience, the reference materials are is numerically referenced and grouped in the appended bibliography.

Capillaries within the brain include a barrier which prevents the delivery of many pharmaceutical agents to the brain. This blood-brain barrier (BBB) is present in both normal and abnormal brain tissue. The treatment of brain tissue abnormalities, such as tumors, require that the neuropharmaceutical agent be preferentially directed to the abnormal tissue. Accordingly, there has been a great deal of interest in developing techniques which are capable of opening the blood-brain barrier to allow transport of neuropharmaceutical agents to the brain (1, 2, 3, 4 and 5). None of these methods, however, are capable of selectively opening the blood-brain barrier only in the abnormal brain while leaving the blood-brain barrier in the normal brain intact.

In previous studies, it was demonstrated that intracarotid infusion of leukotriene $C_4(LTC_4)$ selectively increases the permeability in brain tumor capillaries without affecting the permeability in normal brain capillaries (6–9). The effect of $LTC_4$ on brain tumor capillaries is, however, limited to small molecules and it can only slightly increase the permeability of those small molecules in abnormal brain tissue. Accordingly, $LTC_4$ does not significantly increase the delivery of some water soluble drugs to brain tumors (10–13).

Bradykinin is a naturally occurring peptide formed from a plasma protein, high molecular weight kininogen by the action of kallikrein. Bradykinin is a very powerfull vasodilator that increases capillary permeability. In addition, bradykinin constricts smooth muscle and stimulates pain receptors. Bradykinin may reduce cerebral blood flow (14, 15) and in high doses will induce breakdown of the normal blood-brain barrier (16). U.S. Pat. No. 5,112,596 discloses the intravenous administration of bradykinin and bradykinin agonists to provide a general increase of blood-brain barrier permeability.

U.S. Pat. Nos. 5,434,137 and 5,527,778 disclose the use of bradykinin and bradykinin analogs to selectively increase the permeability of abnormal brain tissue capillaries to both low and high molecular weight neuropharmaceutical and neurodiagnostic agents. The methods disclosed in these patents utilize intracarotid artery infusion of low doses of bradykinin or a bradykinin analog to achieve the desired selective delivery of neuropharmaceutical agents to abnormal brain tissue. The mechanism by which bradykinin achieves such selective action on abnormal brain tissue capillaries has not been well understood.

In view of the above, there is a continuing need to develop methods for selectively opening abnormal brain tissue capillaries in order to allow selective passage of neuropharmaceutical agents into abnormal brain tissue without increasing the permeability of the normal blood-brain barrier.

SUMMARY OF THE INVENTION

In accordance with the present invention, it was discovered that cyclic guanoine monophosphate specific phosphodiesterase inhibitors, when introduced in combination with bradykinin or bradykinin analogs, provide an increase in the selective permeability of abnormal brain tissue capillaries above and beyond that obtainable with bradykinin or bradykinin analogs alone. The use of cyclic GMP specific phosphodiesterases is especially effective in increasing the bradykinin-based permeability of brain tumors which have high rates of metabolism for cyclic GMP. It is believed that bradykinin increases the production of cyclic GMP in abnormal tissues and the resultant increase in cyclic GMP levels produces increased permeability in the tissue microvessels. Accordingly, the effect of bradykinin and its analogs can be increased and extended by treating the tissue with cyclic GMP specific phosphodiesterase inhibitors or any other compound which reduces the inactivation of cyclic GMP.

The present invention provides for pharmaceutical preparations in which bradykinin or a bradykinin analog is combined with one or more cyclic GMP specific phosphodiesterase inhibitors. The preparations generally include a pharmaceutically acceptable carrier and may even include a neurodiagnostic or neuropharmaceutical agent. The pharmaceutical preparations can be administered intravenously or via the carotid artery.

The above-described and many other features and attendant advantages of the present invention will become better understood by reference to the following detailed description when taken in conjunction with the accompanying drawings.

The abbreviations used in the drawings are as follows:

BST=brain surrounding tumor;

Ips Co=ipsilateral cortex;

Contra Co=contralateral cortex;

Ips Whi=ipsilateral white matter;

Contra Whi=contralateral white matter;

Ips BG=ipsilateral basal ganglia;

Contra BG=contralateral basal ganglia;

*=significantly different from PBS control group at $p<0.01([^{14}C]$-dextran, $p<0.01([^{14}C]$-AIB);

**=significantly different from bradykinin infusion group at $p<0.05$ in $[^{14}C]$-AIB;

+=significantly different from PBS control group at $p<0.05([^{14}C]$-AIB);

++=significantly different from bradykinin infusion group at $p<0.05([^{14}C]$-AIB).

DETAILED DESCRIPTION OF THE PREFERRED EMBODIMENTS

The present invention is directed to methods and compositions which are useful in selectively opening abnormal brain tissue capillaries of a mammal in order to allow selective passage of a wide variety of pharmaceutical and diagnostic agents into abnormal brain tissue. The invention provides for the selective introduction of both low and high molecular weight neuropharmaceutical and neurodiagnostic agents into the abnormal brain tissues. The present invention may be used to treat a wide variety of abnormal brain tissue including brain tumors, abnormal tissues resulting from multiple sclerosis, ischemia and cerebral abscess. The invention is also applicable to brain tissue which is inflamed, infected or degenerated due to any number of different diseases. Examples of specific types of abnormal brain tissue include gliomas, metastatic brain tumors, head injury, meningitis, brain abscess, multiple sclerosis, subarachnoid hemorrhage.

The present invention is an improvement upon existing methods which are based upon the infusion of bradykinin or a bradykinin analog into the bloodstream of a mammal to provide opening of abnormal brain tissue capillaries. The improvement involves administering a cyclic GMP specific phosphodiesterase inhibitor to the mammal as part of the treatment protocol. It was discovered that introducing a cyclic GMP specific phosphodiesterase inhibitor into the bloodstream prior to and/or during administration of the bradykinin or bradykinin analog resulted in an increase in selective permeability of abnormal brain tissue.

The amount of bradykinin or bradykinin analog infused into the bloodstream depends in part upon the route of administration. Intravenous administration follows dosage levels along the lines set forth in U.S. Pat. No. 5,112,596. When bradykinin or bradykinin analogs are introduced into the carotid artery, the dosage levels are decreased substantially in accordance with the dosage levels set forth in U.S. Pat. No. 5,527,778. The infusion of a cyclic GMP specific phosphodiesterase inhibitor increases selective permeability for both intravenous and intracarotid artery delivery of bradykinin. The use of cyclic GMP specific phosphodiesterase inhibitors was found to be especially useful in connection with the delivery of bradykinin or bradykinin analogs into the carotid artery.

Zaprinast (2-(2-propyloxyphenyl)-8-azapurin-6-one) is a preferred cyclic GMP specific phosphodiesterase inhibitor. Zaprinast is widely available and has been studied extensively. See Reference Nos. 23, 24, 25 and 26. Zaprinast is also identified as M&B 22948. In addition to Zaprinast, other suitable cyclic GMP specific phosphodiesterase inhibitors include MY-5445 (1-(3-chlorophenyl-amino-4-phenylplithalazine) (27) and dipyridamole (28).

The following description will refer to zaprinast as the preferred cyclic GMP specific phosphodiesterase inhibitor. It will be understood by those skilled in the art that any of the other inhibitors having similar properties may be used in place of zaprinast.

The dosage of zaprinast which is required in order to increase the permeability induced by bradykinin/bradykinin analogs will vary depending upon numerous different factors. These include the type of abnormal tissue being treated, the route of administration of both the bradykinin/bradykinin analog and zaprinast as well as other factors including relative size of the abnormal tissue. The following information is provided as a guide with it being understood by those skilled in the art that final preferred dosages will be established by routine procedures which are typically used in establishing the correct dose for any pharmaceutical or diagnostic agent.

It is preferred that zaprinast be administered to the bloodstream of the patient just prior to and during administration of the bradykinin/bradykinin analog. Although the bradykinin/bradykinin analog and zaprinast may be administered separately, it is preferred that they be mixed and infused together. For infusion into the carotid artery, it is preferred that the bradykinin/bradykinin analog dosage be between 0.001 µg/kg bodyweight/minute and 20 µg/kg bodyweight/minute. The preferred dosage levels for zaprinast is 0.05 mg/kg bodyweight/minute and 30 mg/kg bodyweight/minute. When introduced intravenously, the preferred dosage levels for bradykinin/bradykinin analog is 0.003 µg/kg/bodyweight/minute to 50 µg/kg bodyweight/minute. The corresponding intravenous dosage levels for zaprinast is preferably between about 0.10 mg/kg/bodyweight/minute and 50 mg/kg bodyweight/minute.

A preferred mode of treatment is to introduce both the bradykinin/bradykinin analog and zaprinast simultaneously into the carotid artery over a period of about 5 to 20 minutes. During this time period, a neuropharmaceutical agent may be introduced intravenously or through the carotid artery. The selectively opened abnormal brain tissue capillaries allow passage of the neuropharmaceutical agent into the abnormal brain tissue for treatment. It is preferred that the total amount of bradykinin/bradykinin analog which is infused into the carotid artery during any single treatment be kept below about 400 µg/kg bodyweight with the total amount of zaprinast being kept below about 2 grams. For intravenous treatments, it is preferred that the infusion period be on the order of about 5 minutes to 30 minutes with total dosage amounts ranging from about 0.03 µg to 1.5 mg/kg for bradykinin/bradykinin analog, and from about 3 mg/kg to 1500 mg/kg for zaprinast.

Any of the well known neuropharmaceutical agents may be administered in accordance with the present invention. Low molecular weight (100–20,000) as well as high molecular weight (about 20,000 to 100,000) neuropharmaceutical agents may be used. In addition to neuropharmaceutical agents, diagnostic agents may be used including imaging or contrast agents. Exemplary diagnostic agents include substances that are radioactively labeled such as 99-Tc glucoheptonate, gallium-ethylene diamine tetracetive acid (EDTA), ferrous magnetic or jointed contrast agents. Exemplary neuropharmaceutical agents include antibiotics, adrenergic agents, anticonvulsants, nucleotide analogs, chemotherapeutic agents, anti-trauma agents and other classes of agents used to treat or prevent neurological disorders. Specific neuropharmaceutical agents which can be administered into abnormal brain tissue in accordance with the present invention include cisplatin, carboplatin, tumor necrosis factor-a (TNF-a), methotrexate, 5-FU, amphotericin, immunotoxins, boron compounds, monoclonal antibodies and cytokines, such as interferons, interleukins, transforming growth factors, oligonucleotides, virus for gene therapy.

In the preferred method, the bradykinin/bradykinin analog and zaprinast are administered into the carotid artery by any of the well known infusion techniques. For example, the bradykinin/bradykinin analog and zaprinast are directly infused into the carotid artery by following the procedure used for cerebral angiography where a catheter is inserted into the femoral artery and directed into the internal carotid artery or a more distal cerebral artery using fluoroscopic X-rays. Administration intravenously is by conventional procedures which are well-known.

Bradykinin is a naturally occurring peptide comprised of nine amino acids. The structure of bradykinin and methods for isolating and purifying bradykinin are well-known. Analogs of bradykinin include related peptide structures which exhibit the same properties as bradykinin but have modified amino acids or peptide extensions on either terminal end of the peptide. Examples of bradykinin analogs include [phe$^8$ (CH$_2$—NH) Arg$^9$]—bradykinin, N-acetyl [phe$^8$ (CH$_2$—NH Arg$^9$] bradykinin and desArg$^9$-bradykinin. A preferred analog is known as RMP-7 or A-7 which is identified in U.S. Pat. No. 5,268,164 and PCT Application No. WO92/18529.

The bradykinin/bradykinin analog and zaprinast are preferably infused in the form of a pharmaceutical solution having a 0.09 percent phosphate buffered saline solution as the carrier. The concentration of bradykinin in the solution is 10–40 $\mu$g/ml with the preferred concentration of zaprinast being on the order of 1 to 10 mg/ml for carotid artery administration. For intravenous administration, the concentration of bradykinin/bradykinin analog is preferably between about 15 $\mu$g/ml to 50 mg/ml with the preferred concentration of zaprinast being on the order of 2 mg/ml to 15 mg/ml. Zaprinast is not soluble directly in saline. Accordingly, it is preferred that the pharmaceutical solution be prepared by dissolving zaprinast in 1 M sodium hydroxide to form a concentrated solution of approximately 100 to 500 mg/ml zaprinast. This concentrated solution is then dissolved into phosphate buffered saline (PBS) to the final desired concentration. Bradykinin or the bradykinin analog is then added to the solution to form the final pharmaceutical preparation. The relative concentrations within the pharmaceutical preparation are adjusted as set forth above to provide a solution which is suitable for either carotid artery infusion or intravenous administration.

Although it is possible to administer the neuropharmaceutical agent separately, it is preferred that the neuropharmaceutical agent, when possible, be included in the pharmaceutical solution containing bradykinin/bradykinin analog and zaprinast.

Examples of treatment protocols utilizing the compositions and methods of the present invention are as follows:

EXAMPLE 1

Treatment Of Brain Tumors

For malignant brain tumors having a diameter below about 6 cm, sufficient bradykinin and zaprinast to provide a delivery rate of 20 $\mu$g/kg bodyweight/minute bradykinin and 10 mg/kg bodyweight/minute zaprinast. Carboplatin (antitumor agent) is included in the solution in an amount such that infusion of the solution over a time period of between 5 to 20 minutes will result in a 500 mg dose of carboplatin being administered to the patient. For relatively large tumors, it is preferred that the bradykinin/zaprinast/carboplatin neuropharmaceutical agent be administered into the carotid artery for a period of 5 to 20 minutes. Pharmaceutical preparation is a buffered saline solution having bradykinin and zaprinast concentrations which are sufficient to provide delivery rates of 10 $\mu$g/kg bodyweight/minute bradykinin and 5 mg/kg bodyweight/minute zaprinast. The concentration of carboplatin is sufficient to provide a total dosage of 300 mg.

EXAMPLE 2

Treatment Of Inflamed Brain Tissue

Brain tissue may become infected due to a variety of different causative factors. For example, infected brain tissue may result from AIDS or ear infections. The same basic procedure set forth in Example 1 may be used to treat infected brain tissue except that the neuropharmaceutical agent is changed to one suitable for treating infection. For less serious brain tissue infection, it is preferred to administer the composition intravenously utilizing the same phosphate buffered saline composition set forth in Example 1, except that the pharmaceutical agent added to the preparation is preferably an antibiotic which will be included at a dosage level commensurate with the degree of infection. For more severe infections, the carotid artery infusion protocol is preferred utilizing the compositions set forth in Example 1 which includes an antibiotic instead of the carboplatin anti-tumor agent.

EXAMPLE 3

Demonstration Of Efficacy

Materials and Methods

One hundred seventy-seven (177) female Wister rats, weighing 170–220 g were used for this study. All animal experimentation was conducted in accordance with policies set by the University of California at Los Angeles Chancellor's Animal Research Committee and NIH guidelines.

Tumor Inoculation

RG2 and C6 are cell lines derived from rat gliomas induced by ethylnitrosourea (17,18). The glioma cells were kept frozen until use, then thawed and maintained in a monolayer culture in F12 medium with 10% calf serum. The rats were anesthetized with intra-peritoneal ketamine (50 mg/kg). Glial tumors were implanted into the right hemisphere by intracerebral injections of 1×10$^5$ glioma cells in 5 $\mu$l F12 medium (1.2% methylcellulose) by a Hamilton syringe. The coordinates used were 5 mm lateral to the bregma, and 4.5 mm deep to the dural surface.

Animal Preparation

Seven or eight days after tumor implantation, the rats were anesthetized with intra-peritoneal urethane (1 g/kg)

and a polyethylene catheter was inserted retrograde through the external carotid artery to the common carotid artery bifurcation ipsilateral to the tumor. The external carotid artery and pterygopalatine artery were then ligated. Both femoral veins were cannulated for administration of drugs or tracers. One femoral artery was cannulated to monitor systemic blood pressure and the other femoral artery was cannulated to withdraw arterial blood. Body temperature was maintained at 37° C. and arterial blood gases, blood pressure, and hematocrit were monitored.

Dose Determinations and Preparations of the Drugs

In preliminary studies 10, 20 or 30 mg/kg/minute of zaprinast (Sigma Chemical Co., St. Louis, Mo.), was infused into the carotid artery for 15 minutes and physiological parameters were monitored. Serious systemic hypotension and respiratory irregularity occurred at the 30 mg/kg/minute dose. Therefore, 20 mg/kg/minute zaprinast was infused for these examples. Since zaprinast is not soluble in saline, it was prepared as a concentrated solution (250 mg/ml) in 1 M NaOH and dissolved into phosphate buffered saline (PBS) final concentration 5 mg/ml. The diluted solution was adjusted to pH 7.5.

Effect of Bradykinin on BTB Permeability

The tumor-implanted rats were grouped by tracers and by tumor types. Bradykinin (Sigma Chemical Co., St. Louis, Mo.) or PBS (control) was infused into the right carotid artery at a rate of 53.3 $\mu$l/minute (10 $\mu$g/kg/minute) for 15 minutes. In regional permeability studies, 5 minutes after the start of the intracarotid infusion, 100 mCi/kg of [$^{14}$C]-AIB (MW 103, Dupon-New England Nuclear Co., Boston, Mass.) or [$^{14}$C]-Dextran (MW 70,000, Dupon-New England Nuclear Co.) was injected as an intravenous bolus. A peristaltic withdrawal pump was used to withdraw femoral arterial blood at a constant rate of 0.083 $\mu$l/minute immediately after the injection of the tracer for the determination of serum radioactivity. Fifteen minutes after the start of intracarotid infusions, the animals were killed by decapitation and the brains were rapidly removed and frozen.

Effect of zaprinast on BTB Permeability Enhanced by Bradykinin

Bradykinin, zaprinast or bradykinin mixed with zaprinast was infused into the right carotid artery at a rate of 53.3 $\mu$l/minute for 15 minute. The rate of infusion of bradykinin and zaprinast was 10 $\mu$g/kg/minute and 1.67 mg/kg/minute (20 mg/kg total dose) respectively. Injection of tracer, withdrawing of arterial blood, and other protocols were in the same manner as described above.

The duration of the effect of the intracarotid bradykinin with or without zaprinast infusion in RG2 glioma was examined at three different periods by changing the time of [$^{14}$C]-dextran injection relative to intracarotid infusion of bradykinin with or without zaprinast.

The frozen brains were mounted onto pedestals with M-1 embedding matrix (Lipshaw, Pittsburgh, Pa.) and 20 $\mu$m coronal sections were cut with a cryotome. The sections were thawmounted onto cover slips and autoradiograms were generated by co-exposing the sections on Kodak XAR-5 film with tissue calibrated [$^{14}$C]-standards (Amersham, Arlington Heights, Ill.) for 2 weeks. The sequential section was stained with hematoxylin for the correlation of areas of histologically verified tumor areas with autoradiograms. The regional radioactivity was measured in the tumor, BST (areas within 2 mm distance from the border of the tumor), right cortex (ipsilateral cortex), left cortex (contralateral cortex), right white matter, left white matter, right basal ganglia, and left basal ganglia. Quantitative analysis of the regional radioactivity was performed using a computer (Power Macintosh 7100) and the software, Image 1.55 (NIH).

For quantitative autoradiographic examination, the regional permeability in the brain and tumor tissues were expressed by the unidirectional transfer constant, Ki value ($\mu$l/g/minute) which was determined as described in References 21, 22, 23 and 24).

For all tracers, statistical comparison of regional Ki values or blood volume between same regions with/without bradykinin or zaprinast were determined using analysis of variance (ANOVA) followed by non-parametric analysis of Mann-Whitney's U test. A probability of <0.05 was considered significant.

Results

Effects of Bradykinin and/or zaprinast on Physiological Parameters

Physiological parameters, which included systemic blood pressure, arterial blood gas, and hemoglobin concentration were not significantly changed by intracarotid bradykinin infusion at a rate of 10 $\mu$g/kg/minute during the experiments. The physiological parameters were not significantly changed in any of the experimental conditions except for zaprinast infusion. Intracarotid infusion of zaprinast with bradykinin significantly decreased mean arterial blood pressure in a dose dependent manner. Mean arterial blood pressures were decreased 27.0 ±5.7% by intracarotid infusion of zaprinast (1.67 mg/kg/minute, 15 minutes). zaprinast did not change blood gas parameters or hemoglobin concentration.

Blood Volume in Tumor and Normal Brain

The blood volume ($\mu$l/g) for quantitative examination of permeability was calculated using a graphic method as previously described. The blood volume in RG2 tumors in the saline group, the bradykinin group, the bradykinin with zaprinast group were 12.6, 14.4, 13.8 and 14.8 $\mu$l/g respectively. The blood volume in RG2 tumors in the saline group, the bradykinin group, the bradykinin with zaprinast group were 12.0, 13.2 and 12.7 $\mu$l/g respectively. The tumor or normal brain blood volumes were not significantly different among treatment groups.

Regional Permeability

Figure 1:
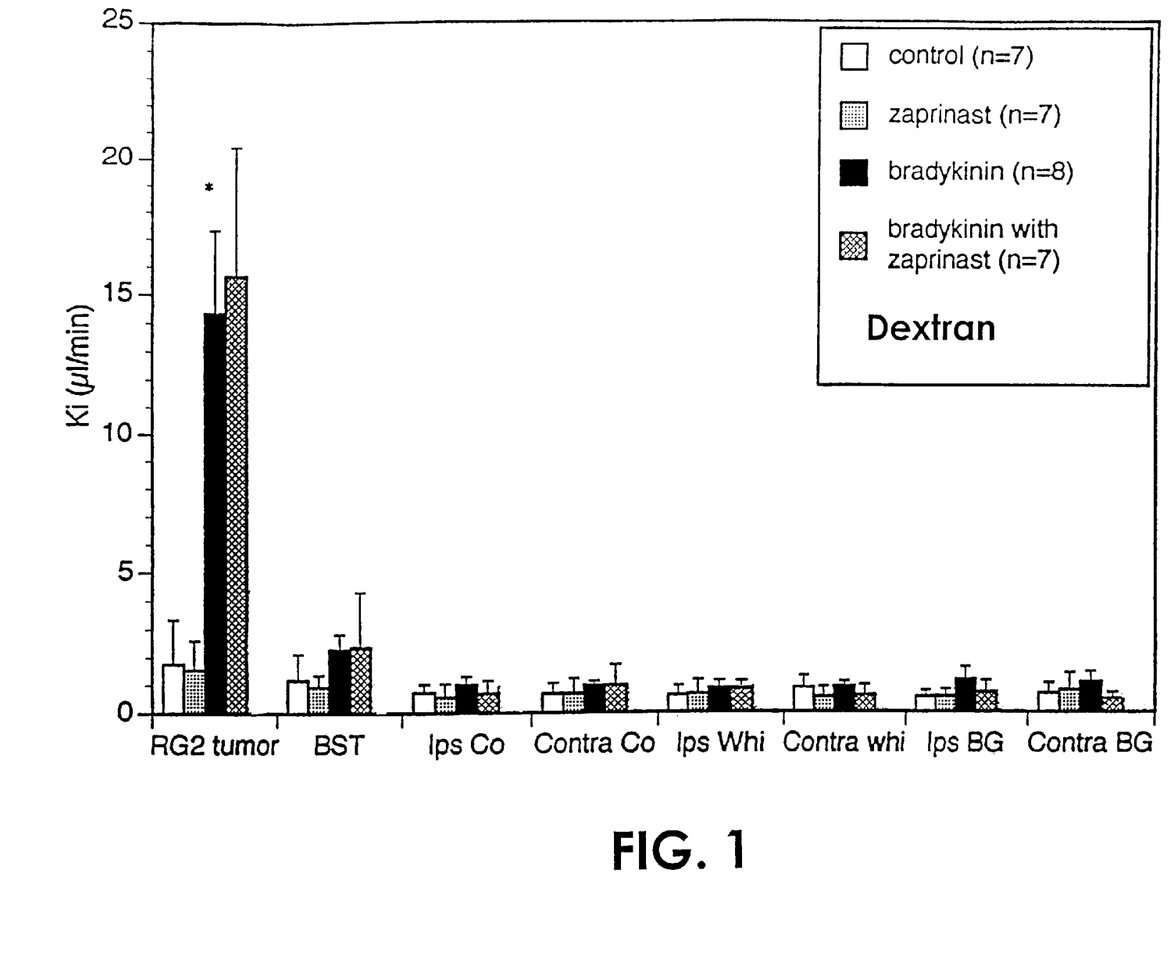
FIG. 1 is a graphical depiction of results of tests showing the increase in selective introduction of dextran (MW 70,000) into RG2 brain tumors which occurs when a cyclic GMP specific phosphodiesterase inhibitor (zaprinast) is added to bradykinin.
Figure 2:
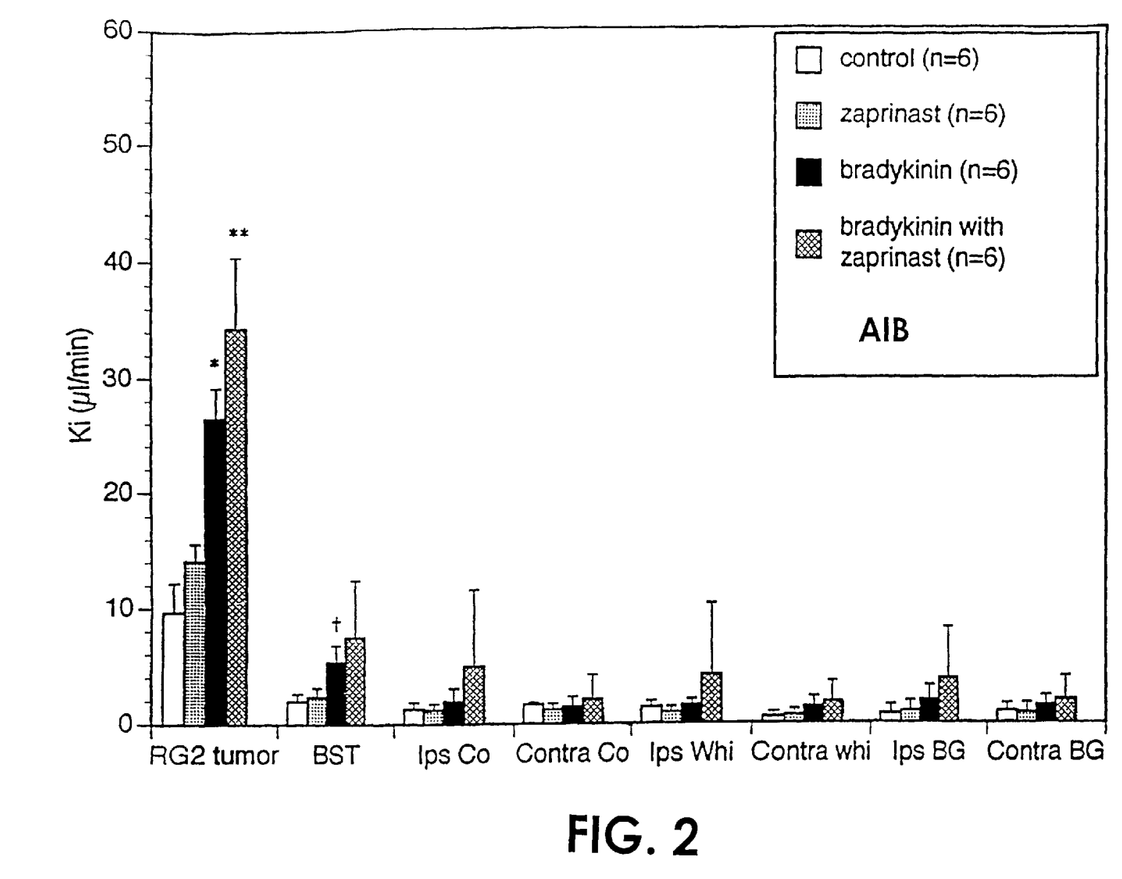
FIG. 2 is a graphical depiction of results of tests showing the increase in selective introduction of AIB (MW 103) into RG2 brain tumors which occurs when a cyclic GMP specific phosphodiesterase inhibitor (zaprinast) is added to bradykinin.

RG2 gliomas:

The Ki values were calculated using the method described in previous studies (23). The transfer constant, Ki, in tumors for [$^{14}$C]-dextran (MW 70,000) after bradykinin infusion (n=8) was 8.4-fold higher than in controls (n=7) (Mean±standard deviation, 14.33±2.96 vs. 1.77±1.57; p<0.01) (see FIG. 1). The transport in tumors for [$^{14}$C]-AIB (MW 103) after infusion of bradykinin (n=6) was also increased compared to controls (n=6) (26.46±2.64 vs. 9.68±2.51; p<0.01) (FIG. 2). Permeability in brain within 2 mm of the tumor was increased since BST tissue may be affected by tumor compression and vasoactive agents released directly by tumors. The Ki for AIB was significantly increased in BST after bradykinin infusion (5.31±1.50 vs. 2.68±1.26; p<0.05) but the Ki for dextran was not significantly increased in BST. The bradykinin infusion did not increase transport of either tracer in any other normal brain regions tested.

Intracarotid infusion of zaprinast alone did not increase the Ki values in RG2 tumors for both tracers. The combined administration of zaprinast and bradykinin significantly increased the Ki value in tumors for AIB compared to the bradykinin infusion alone (34.27±6.06 vs. 26.46±2.64; p<0.05) (FIG. 2). The combined bradykinin-zaprinast treatment provided less of an increase in Ki values for dextran compared to AIB (see FIG. 2). In non-tumor regions, the Ki of either tracers showed no significant increases (see FIGS. 1 and 2).

The effect of intracarotid infusion was examined at three different time periods with [$^{14}$C]-dextran. The effect of bradykinin alone and bradykinin combined with zaprinast on tumor permeability was diminished 20 minutes after stopping the intracarotid infusion. However, 10 minutes after stopping the intracarotid infusion, [$^{14}$C]-dextran uptake into the tumor was significantly higher in the bradykinin with zaprinast group compared to the bradykinin alone group (9.40±3.13 vs. 3.89±0.74; p<0.01).

Figure 3:
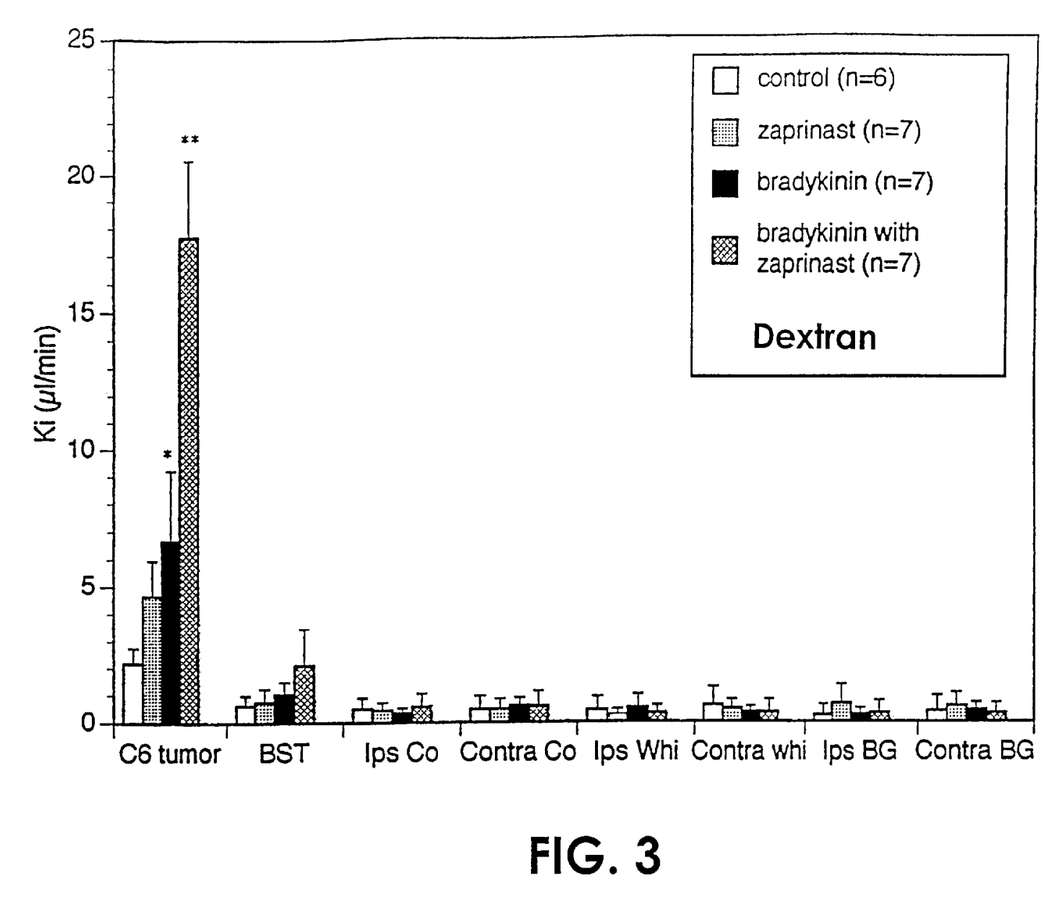
FIG. 3 is a graphical depiction of results of tests showing the increase in selective introduction of dextran (MW 70,000) into C6 brain tumors which occurs when a cyclic GMP specific phosphodiesterase inhibitor (zaprinast) is added to bradykinin.

C6 gliomas:

The Ki in tumors for [$^{14}$C]-dextran after bradykinin infusion (n=8) was 3.1-fold higher than in controls (n=7) (6.67±2.54 vs. 2.18±0.57; p<0.02) (see FIG. 3). The transport in tumors for [$^{14}$C]-AIB after infusion of bradykinin (n=6) was also increased compared to controls (n=6) (34.84±8.14 vs. 16.35±5.97; p<0.01) (see FIG. 4). The bradykinin infusion did not increase transport for either tracer in non-tumor regions (see FIGS. 3 and 4)

Figure 4:
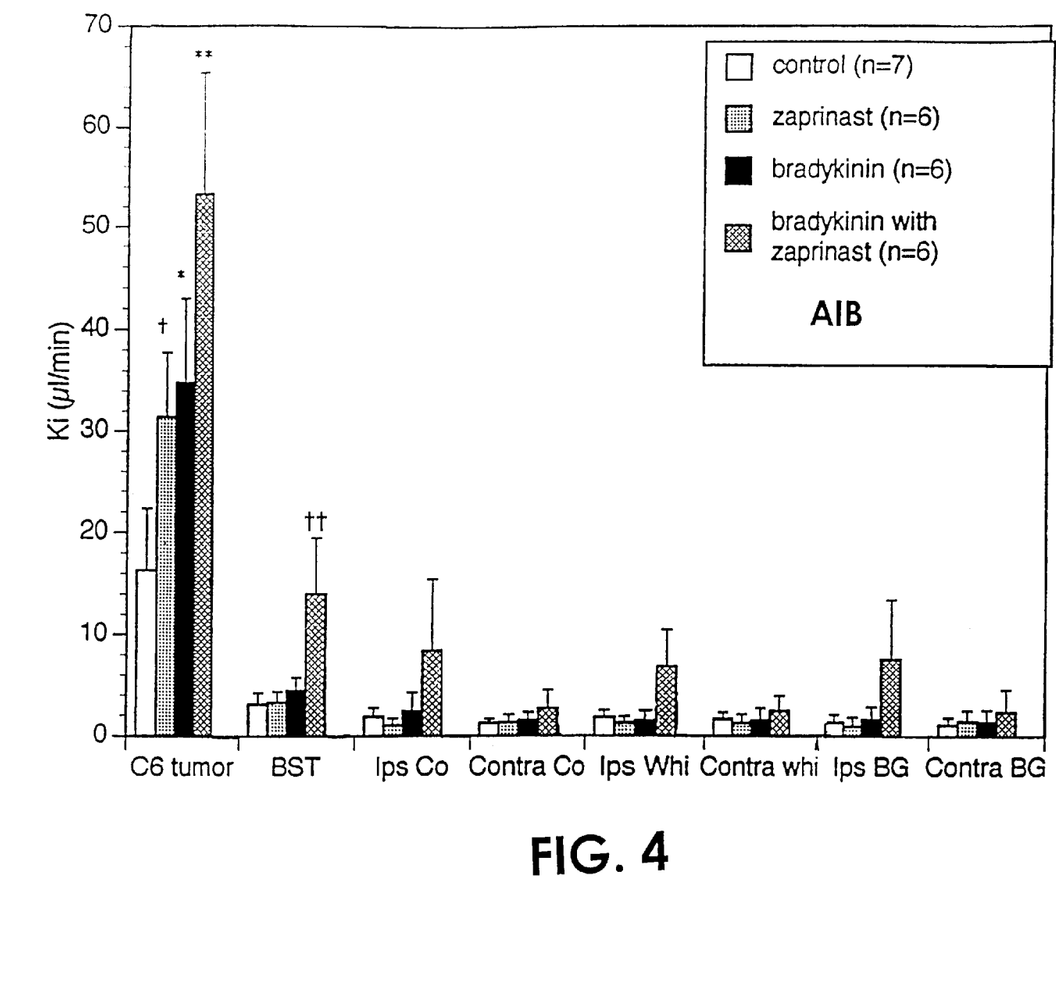
FIG. 4 is a graphical depiction of results of tests showing the increase in selective introduction of AIB (MW 103) into C6 brain tumors which occurs when a cyclic GMP specific phosphodiesterase inhibitor (zaprinast) is added to bradykinin.
Figure 5:
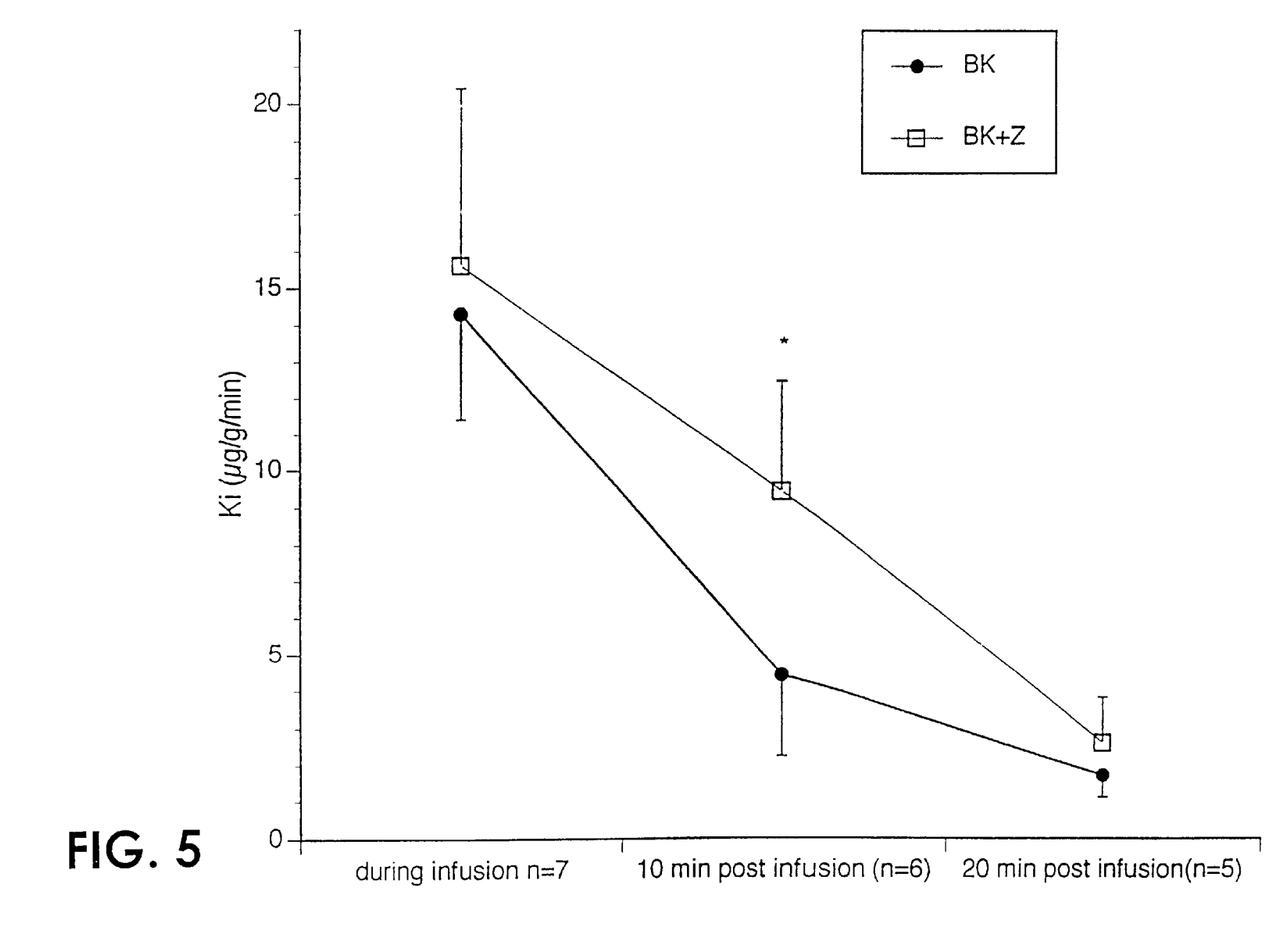
FIG. 5 depicts the graphical results of time course studies showing the permeability levels of bradykinin with or without a cyclic GMP specific phosphodiesterase inhibitor (zaprinast) in the tumor region. The permeability (Ki) values in tumors were examined at three different time periods. Mean±standard deviation (SD) of Ki values are shown. The bradykinin effect was significantly prolonged by the zaprinast at 10 minutes after infusion. After 20 minutes, the increased permeability benefits provided by zaprinast were negligible.

Intracarotid infusion of zaprinast alone increased the Ki values in C6 tumors for [$^{14}$C]-AIB (16.35 6.00 vs. 31.45 6.36; p<0.01), but not for [$^{14}$C]-dextran (see FIGS. 3 and 4). Simultaneous infusion of zaprinast and bradykinin significantly increased the Ki value in tumors for both tracers compared to the bradykinin infusion alone (17.69 2.54 vs. 17.69 2.82; p<0.01 dextran, 53.29 12.25 vs. 34.84 8.14; p<0.05 AIB), furthermore, combined treatment significantly increased the Ki for AEB in BST (see FIGS. 3 and 4). In other non-tumor regions, the Ki for either tracer showed no significant differences between the combined treatment group and the group treated by bradykinin alone.

Having thus described exemplary embodiments of the present invention, it should be noted by those skilled in the art that the within disclosures are exemplary is only and that various other alternatives, adaptations and modifications may be made within the scope of the present invention. Accordingly, the present invention is not limited to the above preferred embodiments, but is only limited by the following claims.

BIBLIOGRAPHY

1. Kumagai, A. K., Eisenberg, J. B., Pardridge, W. M., "Absorptive-mediated endocytosis of cationized albumin and a b-endorphin-cationized albumnin chimeric peptide by isolated brain capillaries. Model system of blood-brain barrier transport," *J. Biol. Chem.* 262:15214–15219, 1987.
2. Neuwelt, E. A., Barnett, P. A., McCornick, C. I. et al., "Osmotic blood-brain barrier modification: monoclonal antibody, albumin, and methotrexate delivery to cerebrospinal fluid and brain," *Neurosurgery* 17:419–423, 1985.
3. Neuwelt, E. A., Hill, S. A., Frenkel, E. P., "Osmotic blood-brain barrier modification and combination chemotherapy: concurrent tumor regression in areas of barrier opening and progression in regions distant to barrier opening," *Neurosurgery* 15:362–366, 1984.
4. Pardridge, W. M., Kumagai, A. K., Eisenberg, J. B., "Chimeric peptides as a vehicle for peptide pharmaceutical delivery through the blood-brain barrier," *Biochem. Biophys. Res. Commun.* 146:307–313,1987.
5. lomiwa, K., Hazama, F., Mikawa, H., "Neurotoxicity of vincristine after osmotic opening of the blood-brain barrier," *Neuropathol. Appl. Neurobiol.* 9:345–354, 1983.
6. Black, K. L., Betz, A.L ., Ar, D. B., "Leukotriene $C_4$ receptors in isolated brain capillaries," *Adv. Prostaglandin Thromboxane Leukotriene Res.* 17:508–511, 1987.
7. Black, K. L., Hoff, J. T., "Leukotrienes and blood-brain barrier permeability," *Cereb Flow Metab.* 5 (Suppl) :263–264, 1985.
8. Black, K. L., Hoff, J. T., "Leukotrienes increase blood-brain barrier permeability following intraparenchymal injections in rats," *Ann. Neurol.* 18:349–351, 1985.
9. Black, K. L., Hoff, J. T., McGillicuddy, J. E. et al., "Increased leukotriene $C_4$ and vasogenic edema surrounding brain tumors in humans," *Ann. Neurol* 19:592–595, 1986.
10. Black, K. L., Chio, C. C., "Increased opening of blood-brain tumor barrier by leukotriene $C_4$ is dependent on size of molecules," *Neurological Res.* 74:402–404, 1982.
11. Black, K. L., King, W. A., Ikezaki, K., "Selective opening of the blood tumor barrier by intracarotid infusion of leukotriene $C_4$," *J. Neurosurg.* 72:912–916, 1990.
12. Baba, T., Black, K. L., Ikezaki, K., Chen, K., Becker, D. P., "Intracarotid infusion of leukotriene $C_4$ selectively increases blood-brain permeability after focal ischemia in rats," *J. Cereb. Blood Flow Metab.* 11, No. 4, 1991.
13. Chio, C. C., Baba, T., Black, K. L., "Selective blood-tumor barrier description by leukotrienes," *J. Neurosurg.* 77, 1992.
14. Yong, T. et al., *Circ. Res.* 70, 952, 1992.
15. Alvarez, A. L. et al., *Clin. Sci.* 82, 513, 1992.
16. Raymond, J. J., Robertson, D. M., Dinsdale, H. B., *Can. J. Neurol. Sci.* 13, 214, 1986.
17. Ko, L., Koestner, A., Wechsler, W., *Acta Neuropathol.* 51, 23–31, 1980.
18. Wechsler, W., Ramadan, M. A., Gieseler, A. *Naturwissenschaften* 59, 474–478, 1972.
19. Ziylan, Y. Z., LeFauconnier, J. M., Bernard, G., Bourre, J. M., *Neurochem.* 51, 1338–1342, 1988.
20. Ohno, K., Pettigrew, K. O., Rapoport, S. T., *Am. J. Physiol.* 253, H299–H307, 1978.
21. Inamura, T., Black, K., *J. Cereb. Blood Flow Metab.* 14, 862–870, 1994.
22. Inamura, T., Nomura, T., Bartus, R., Black, K., Neurosurg. 81, 752–758, 1994.
23. Gillespie, P. G., Beavo, J. A., "Inhibition and stimulation of photoreceptor phosphodiesterases by dipyridamole and M&B 22,948," *Mol Pharmacol* 365, 773–781, 1989.
24. Burns, F., Roger, I. W., Pyne, N. J., "The catalytic subunit of protein kinase A triggers activation of the type V cyclic GMP-specific phosphodiesterase from guinea-pig lung," *Biochem J.* 283 Pt. 2, 487–491, 1992.
25. Dundore, R. L. Clas, D. M., Wheeler, L. T. , Habeeb, P. G., Bode, D. C., Buchholz, R. A., Silver, P. J., Pagani, E. D., "zaprinast increases cyclic GMP levels in plasma and in aortic tissue of rats," *Eur. J. Pharmacol.* 249 3, 293–297, 1993.
26. Steiner, A. L., Parker, C. W. & Kipnis, D. M. (1972) *J. Biol. Chem,* 247. 1106–1113.
27. Busse, R., Mulsh, A., Fleming, I. & Hecker, M. (1993) Circulation (Suppl V), 87 V18–V25.
28. Fray, A., Johns, A., Adams, D. J., Ryan, U. S. & Vanbreemen, C. (1989) Pflugars Arch, 414. 377–384.

What is claimed is:

1. The pharmaceutical preparation adapted for use in increasing the selective permeability of abnormal brain tissue capillaries of a patient, said preparation comprising:
    bradykinin or a bradykinin analog;
    cyclic GMP specific phosphodiesterase inhibitor; and
    a sufficient amount of a pharmaceutically acceptable carrier to provide a pharmaceutical preparation which can be introduced into the blood stream of a mammal wherein the concentration of bradykinin or bradykinin analog in said pharmaceutical preparation is between 10 μg/ml to 50 mg/ml and the concentration of cyclic GMP specific phosphodiesterase between 1 mg/ml and 15 mg/ml.

2. The pharmaceutical preparation according to claim 1 wherein said preparation is adapted for carotid artery administration and wherein the concentration of bradykinin or bradykinin analog in said pharmaceutical preparation is between 10 µg/ml to 40 µg/ml and the concentration of cyclic GMP specific phosphodiesterase is between 1 mg/ml and 10 mg/ml.

3. The pharmaceutical preparation according to claim 1 wherein said preparation is adapted for intravenous administration and wherein the concentration of bradykinin or bradykinin analog in said pharmaceutical preparation is between 15 µg/ml to 50 mg/ml and the concentration of cyclic GMP specific phosphodiesterase is between 2 mg/ml and 15 mg/ml.

4. The pharmaceutical preparation according to claim 1 wherein said cyclic GMP specific phosphodiesterase inhibitor is selected from the group consisting of 2-(2-Propyloxyphenyl)-8-azapurin-6-one-1-(3-Chlorophenyl-amino)-4-phenylplithalazine and dipyridamole.

5. The pharmaceutical preparation according to claim 4 wherein said cyclic GMP specific phosphodiesterase inhibitor is 2-(2-Propyloxyphenyl)-8-azapurin-6-one.

6. A pharmaceutical preparation according to claim 1 which comprises bradykinin.

7. The pharmaceutical preparation according to claim 6 wherein said cyclic GMP specific phosphodiesterase inhibitor is 2-(2-Propyloxyphenyl)-8-azapurin-6-one.

8. A pharmaceutical preparation according to claim 1 which further comprises a neuropharmaceutical or neurodiagnostic agent.

9. A pharmaceutical preparation according to claim 1 wherein said pharmaceutically acceptable carrier is phosphate buffered saline.

10. The method for treating abnormal brain tissue present in a mammal with a neuropharmaceutical or neurodiagnostic agent, said method comprising the steps of:
   administering bradykinin or bradykinin analog into the blood stream of said mammal;
   simultaneously administering a cyclic GMP specific phosphodiesterase inhibitor into the blood stream of said mammal; and
   administering an effective amount of a neuropharmaceutical or neurodiagnostic agent into said bloodstream, wherein said bradykinin or bradykinin analog and said cyclic GMP specific phosphodiesterase are administered into said blood stream in an amount which increases the permeability of said neuropharmaceutical or neurodiagnostic agent into said abnormal brain tissue.

11. The method according to claim 10 wherein said cyclic GMP specific phosphodiesterase inhibitor is selected from the group consisting of 2-(2-Propyloxyphenyl)-8-azapurin-6-one, 1-(3-Chlorophenyl-amino)-4-phenylplithalazine and dipyridamole.

12. The method according to claim 11 wherein said cyclic GMP specific phosphodiesterase inhibitor is 2-(2-Propyloxyphenyl)-8-azapurin-6-one.

13. A method according to claim 10 wherein said bradykinin or bradykinin analog is administered intravenously.

14. A method according to claim 13 wherein said bradykinin or bradykinin analog is weight/minute.

15. The method according to claim 10 wherein said bradykinin or bradykinin analog is administered into the carotid artery of said mammal.

16. The method according to claim 15 wherein said bradykinin or bradykinin analog is administered into said carotid artery at a rate of between about 0.001 µg/kg body weight/minute and 20 µg/kg body weight/minute.

17. A method according to claim 15 wherein said cyclic GMP specific phosphodiesterase inhibitor is administered intravenously.

18. A method according to claim 17 wherein said cyclic GMP specific phosphodiesterase inhibitor is administered intravenously at a rate of between about 0.10 mg/kg body weighuminute and 50 mg/kg body weight/minute.

19. The method according to claim 15 wherein said cyclic GMP specific phosphodiesterase inhibitor is administered into said carotid artery.

20. The method according to claim 19 wherein said cyclic GMP specific phosphodiesterase inhibitor is administered into said carotid artery at a rate of between about 0.05 mg/kg body weight/minute and 30 mg/kg body weight/minute.

* * * * *